United States Patent [19]

Pelta

[11] 4,010,368
[45] Mar. 1, 1977

[54] TEST APPARATUS
[75] Inventor: Edmond R. Pelta, Pacific Palisades, Calif.
[73] Assignee: Autoscan, Inc., Culver City, Calif.
[22] Filed: Apr. 28, 1976
[21] Appl. No.: 680,920

Related U.S. Application Data

[63] Continuation of Ser. No. 463,364, April 23, 1974, abandoned.

[52] U.S. Cl. .............................. 250/343; 250/565
[51] Int. Cl.² ................... G01J 1/00; G01N 21/24; G01N 21/26; G01N 21/28
[58] Field of Search .......... 250/343, 344, 345, 346, 250/252, 565; 356/51

[56] References Cited
UNITED STATES PATENTS

| | | | |
|---|---|---|---|
| 3,257,562 | 6/1966 | Erdman et al. | 250/565 |
| 3,790,797 | 2/1974 | Sternberg et al. | 250/345 |

FOREIGN PATENTS OR APPLICATIONS

| | | | |
|---|---|---|---|
| 1,241,612 | 8/1960 | France | 250/343 |

Primary Examiner—Saxfield Chatmon, Jr.
Assistant Examiner—T. N. Grigsby
Attorney, Agent, or Firm—Ellsworth R. Roston

[57] ABSTRACT

A gas analyzer includes a cell adapted to receive a gas mixture and a source of infrared energy adapted to introduce the energy through the cell. A particular gas in the cell absorbs the portion of the energy so that an electrical gas signal is provided which has a magnitude dependent upon the percentage of concentration of the particular gas in the mixture. This gas signal is introduced through a variable resistance and compared with a reference signal to provide an output signal for driving a meter. Prior to the introduction of the gas mixture into the cell, the variable resistance can be adjusted with respect to the reference signal to provide the output signal with a zero magnitude for zeroing the meter. The parameters of the circuit automatically provide for the calibration of the span of the meter with the calibration of the zero of the meter.

8 Claims, 4 Drawing Figures

TEST APPARATUS

This is a continuation of application Ser. No. 463,364, filed Apr. 23, 1974, now abandoned.

BACKGROUND OF THE INVENTION

1. Field of the Invention

This invention relates generally to gas analyzers and more specifically to apparatus and methods for calibrating gas analyzers such as those commonly used for analyzing automotive exhaust.

2. Description of the Prior Art

Gas analyzers of the prior art are used for two general purposes. In some analyzers, it is desired to determine the unknown components of a particular gas mixture. In other gas analyzers, the components are known and it is desired to determine the percentage of concentration of the known gas component within the gas mixture. It is this latter type of analyzer which is commonly used for determining the amount of carbon monoxide, hydrocarbons, carbon dioxide, etc. present in the exhaust gas of an automobile.

It is generally well known that gases have properties for absorbing infrared energy at different wavelengths. Thus, in the first type of analyzer, infrared energy is introduced into the gas mixture and the energy emanating from the gas mixture is measured at different wavelengths. If the output energy is particularly low at a given wavelength, this is indicative of the presence in the gas mixture of the particular gas associated with that given wavelength.

In the second type of analyzer, the concentration of a particular gas in the gas mixture is of interest. In such an analyzer filters are typically used to pass only the energy present at the absorption wavelength associated with the particular gas. In this manner, the energy measurements can be limited to wavelengths narrow enough to exclude other gases which might interfere with the measurement of energy absorbed by the particular gas of interest.

One of the first problems associated with this method of analysis results from the fact that a change in the amount of energy leaving the gas cell can be caused either by the presence of the particular gas within the mixture, or by a change in the amount of energy introduced into the mixture. There has been no simple way to tell which circumstance caused the change in the output energy. This is further complicated by the fact that gas analyzers are typically calibrated as that relatively small changes in output energy correspond to full scale gas concentrations. For this reason, small percentage changes in input energy to a cell could be confused with large concentrations of the particular gas in the mixture. In addition, the amount of infrared energy introduced into the sample varies widely as the temperature of the infrared source changes.

To aid in the elimination of this problem, double beam instruments have been constructed to include one channel containing a gas cell into which the gas mixture is introduced. A reference cell is included in another channel but only air or some inert gas is present in the reference cell. Thus, the energy at the output of the gas cell is related to the amount of energy introduced into the gas cell and is also related to the concentration of the particular gas in the mixture. The energy present at the output of the reference cell is generally related only to the amount of energy entering the reference cell. Thus, the energy signals at the outputs of the cells differ generally only due to the presence of the particular gas in the gas cell.

In these analyzers, the energy signals have been introduced to a detector which provides a composite electrical signal. These composite signal has been processed to produce a reference signal having a magnitude proportional to the energy emanating from the reference cell, and to produce a gas signal having a magnitude proportional to the energy emanating from the gas cell. The gas and reference signals have been introduced to a differential amplifier to produce a difference signal having a magnitude indicative of the loss of energy resulting from the presence of the gas mixture in the gas cell. This loss of energy is dependent upon the volume of the particular gas in the mixture and a meter is typically scaled to provide that indication.

One of the problems associated with the analysis of gas samples results from the fact that the actual percentage of energy absorbed, unfortunately, is not related to the concentration of the gas in the cell, but rather to the number of molecules of gas in the cell. As gas is comprised of free moving molecules which fill a space so that the number of molecules varies significantly with the temperature and pressure of the gas.

The magnitude of the electrical signal also tends to vary with several factors other than the percentage of concentration of the particular gas. For example, the emissivity of the energy source typically varies over a period of time so that the amount of energy entering the cell tends to decrease with age. Also, the sensitivity of the detector varies dramatically with the ambient temperature. Furthermore, the amount of energy absorbed along the optical path tends to increase if dust is permitted to build up in the analyzer. For these reasons, it is desirable to calibrate gas analyzers prior to each use in order to compensate for these factors.

One method for calibrating these instruments has been to initially analyze a gas of known concentration, such as a gas including ten percent carbon monoxide. Analyzers using this method are typically provided with two calibration knobs on the face of the instrument. The first knob is used to zero the meter prior to the introduction of the calibration gas into the instrument. The second knob is used to adjust the span of the meter to indicate the known concentration of the particular calibration gas. Thus, two steps have been used to calibrate the instruments of the prior art.

This calibration method is particularly accurate since it compensates for substantially all of the factors mentioned above. However, this method has been relatively inconvenient. For example, it has been difficult to make the gas available wherever the analyzers have been used. In a laboratory, the calibration gas can be easily stored in proximity to the instrument, but it has been particularly inconvenient to transport this calibration gas for use in the field. Furthermore, the calibration gas has been relatively expensive.

A simpler, although less accurate, method of calibration has involved the use of an obstruction, commonly referred to as an opacity, for use in blocking a known portion of the infrared energy prior to its introduction into the gas cell. This, of course, reduces the magnitude of the energy emanating from the cell. In fact, the amount of the energy reduction is related to the size of the opacity. For calibration purposes, the opacity has been sized to provide the same reduction of energy that a known quantity of gas molecules would provide at a given temperature and pressure. However, the opacity at a constant size corresponds to a different concentration at different altitudes and different temperatures so that this method of calibration does not solve the gas density problem. Nonetheless, if the analyzer is used in a single location and a temperature controlled environment the gas density problem is not of particular significance.

Unfortunately, the placement of the opacity within the infrared energy stream can have different effects if the energy gradient varies across the stream. In some cases, the opacity has been provided with a configuration of a comb to average the energy gradient, but dust collecting on the teeth of the comb has tended to degrade the accuracy of the calibration. Means have been provided to precisely locate the opacity in a specific position within the energy stream. However, these means have been relatively expensive.

As a result, the calibration methods of the prior art have been inconvenient, inaccurate, expensive and time consuming. Furthermore, small deviations in the accuracy of the calibration have produced significant changes in the gas concentrations indicated by the meter.

SUMMARY OF THE INVENTION

The apparatus of the present invention includes an electrical circuit which provides a simple, and accurate method for calibrating a gas analyzer. Without the use of any extended object, such as a calibration gas or an opacity, both the zero and span adjustment of the meter can be made. Furthermore, these two adjustments can be made in a single step. This electrical circuit operates upon the signals following rather than preceding the gas cell to provide a particular signal indicative of no energy loss at the particular wavelength tuned. Thus, this particular signal is provided with the same characteristics which would result from analysis of a gas mixture having a zero percent concentration of the particular gas of interest. This signal can then be used to adjust the zero deflection of the meter. When the instrument is manufactured, the parameters of the electrical circuit can be adjusted so that a meter provides a full scale deflection in response to a signal having a magnitude corresponding to that which would result from a gas of known concentration. After this initial adjustment, the span of the meter is automatically adjusted when the zero of the meter is adjusted. As a result, the calibration circuit can be implemented with only one knob on the face of the analyzer.

In one embodiment, a gas cell and a reference cell provide respective energy signals which can be multiplexed to provide a single composite signal. This composite signal can then be procured to provide a gas signal and a reference signal. The gas signal is introduced through a potentiometer and a particular node into an operational amplifier which drives the meter. A voltage source and resistance provide a constant current which is introduced to the particular node. Dependent upon the impedance of the potentiometer, a portion of this constant current at the particular node will be absorbed by the gas signal. The remaining portion of the constant current will be amplified by the operational amplifier to drive the meter.

Prior to the introduction of the gas sample into the gas cell of the analyzer, the potentiometer can be set so that all of the constant current is absorbed by the gas signal in which case there will be no current to drive the meter. This adjustment therefore provides for the zero adjustment of the meter. With the initial adjustment of the parameters of the electrical circuit, the zero adjustment also calibrates the span of the meter. Automatic gain control means can be provided to maintain the reference signal at a substantially constant value. If the gain correction is made to the composite signal, this control will also reduce the drift of the gas signal resulting from many causes other than gas concentration.

In a further embodiment, the reference signal having a substantially constant magnitude provides the voltage which produces the substantially constant current in the calibration circuit. In such an embodiment even slight variation in the magnitude of the reference signal produce variations in the magnitude of the substantially constant current. As a result, the meter is even less responsive to the drift of the gas and reference signals. This calibration method can be used generally with any analyzer providing a separate gas signal, even those analyzers which have a single gas cell and which do not produce a reference signal.

DESCRIPTION OF PREFERRED EMBODIMENTS

Figure 1:
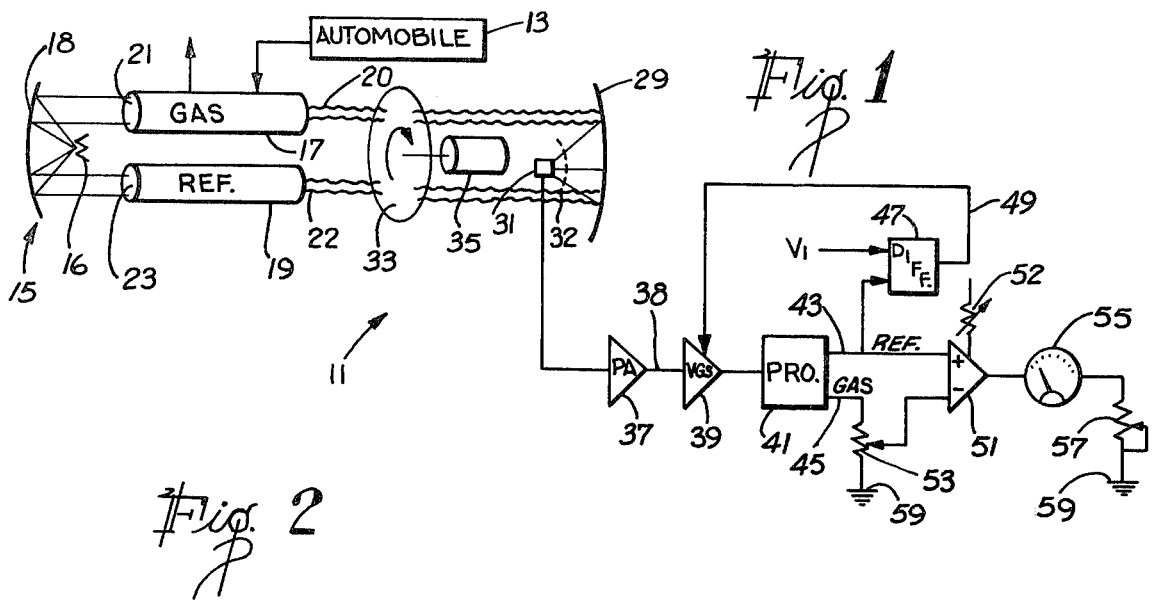
FIG. 1 is a schematic of a gas analyzer including one embodiment of a calibration circuit of the present invention.

A gas analyzer is illustrated schematically in FIG. 1 and designated by the reference numeral 11. It is the purpose of the analyzer 11 not only to detect the presence of a particular gas in a gas mixture but also to determine the percentage of concentration of the particular gas in the gas mixture. For example, the analyzer 11 can be used to detect carbon monoxide, hydrocarbons, carbon dioxide, etc. in the exhaust gas of an automobile 13.

The detection and measurement of the gas is based upon the fact that infrared energy is absorbed when it passes through various gases. The wavelength at which the energy is absorbed is dependent upon the molecular structure of the gas involved and therefore will vary primarily with the particular gas of interest. By measuring the energy level, at a particular wavelength, the degree of absorption can be determined to provide an indication of the percentage of concentration of the particular gas in the gas mixture.

The analyzer 11 includes a source of infrared energy 15 which typically includes a small filament or wire 16 which is electrically heated and located at the focus of a spherical mirror 18. This combination produced essentially parallel infrared light rays which are introduced into a gas cell 17 and a reference cell 19. The cells 17 and 19 can be geometrically identical but the gas cell 15 is adapted to receive the gas to be measured and the reference cell 19 contains only air or an inert gas.

At the end of the gas cell 17 opposite the source of infrared energy 15, the infrared energy passing through the cell 17 will provide a first energy signal 20. This energy signal 20 will have a magnitude which will vary primarily with the concentration of the particular gas in the gas mixture. Similarly, a second energy signal 22 will emanate from the reference cell 19. Without the presence of the gas mixture in the cell 19 however, the magnitude of the signal 22 will generally vary only with those conditions which it has in common with the gas cell 17, such as the cell geometry and the emissivity of the source 15.

A spherical mirror 29 can be positioned in the path of the light signals 20 and 22 emanating from the cells 17 and 19 respectively. It is the purpose of the mirror 29 to converge the light signals 20 and 22 onto a detector 31 positioned at the focus of the mirror 29.

A chopper disk 33, which is typically disposed between the cells 17, 19 and the mirror 29, is rotated by a motor 35. The disk 33 is typically divided into a plurality of sections, each of which treats the signals 20 and 22 differently. Thus, the disk 33 time multiplexes the energy signals 20 and 22 onto the detector 31. The particular treatment given the signals 20 and 22 by the disk 33 will vary the method for demultiplexing the signals in the remaining portions of the circuit.

In order to maintain dynamic balance, the chopper disk 33 in the preferred embodiment is provided with two patterns for rotation so that the pattern of the light signals passing through the disk 33 occurs twice for each rotation of the motor 35. In a preferred embodiment, the motor 35 rotates the disk 33 at approximately 3000 RPM, so the repetition of the chopping pattern occurs 6000 times per minute, or 100 times per second.

In a preferred embodiment, the chopped energy signals passing through the chopper disk 33, are converged by the mirror 29, through an optical filter 32 and onto the detector 35. It is the purpose of the filter 32 to pass only a narrow band of wavelengths including the absorption wavelength of the particular gas of interest. Such an optical filter can be constructed of sapphire, germanium or silicone, for example.

In a preferred embodiment, the detector 35 includes lead selenide photoresistors which are biased by a source of DC current (not shown). As the infrared energy signals fall upon the photoresistors of the detector 35, their resistance decreases to produce an output voltage across the detector 35. This voltage across the detector 35 is quite small and therefore is typically amplified by a preamp 37. The output voltage of the preamp 37 may be held at a constant value such as two volts peak to peak. The electrical signal at the output of the preamp 37 is a composite signal multiplexed or time shared so that it has characteristics dependent upon the magnitudes of both the signals 20 and 22 from the gas cell 17 and the reference cell 19.

The signal at the output of the preamp 37 is introduced on a conductor 38 to a variable gain stage 39 described in greater detail below. Following the variable gain stage, the signal is very precisely controlled to a voltage such as 5 volts peak to peak. This signal is introduced to a signal processor 41, such as a phase detector, which separates the composite signal at the output of the preamp 37 into a reference signal and a gas signal. It is the processor 41 which demultiplexes the composite signal in accordance with the chopping pattern of the disk 33. The reference signal from the processor 41 is introduced onto a conductor 43 and the gas signal from the processor 41 is introduced onto a conductor 45. The reference signal on the conductor 43 has a magnitude which is proportional to the amount of infrared energy emanating from the reference cell 19. The gas signal on the conductor 45 has a magnitude which is proportional to the amount of energy emanating from the gas cell 17.

With the provision of a separate gas signal corresponding to the energy emanating from the gas cell 17 and a separate reference signal corresponding to the energy emanating from the reference cell 19, it is possible to use the reference signal to operate an automatic gain control circuit such as that shown generally at 40.

In the automatic gain control cirucit 40, the reference signal on the conductor 43 can be introduced to a difference circuit 47 along with a reference potential $V_1$. In response to the characteristics of these two input signals, the difference circuit 47 provides a voltage control signal which is introduced on a conductor 49 to the variable gain stage 39. If the DC current component reference signal is more negative than the reference voltage $V_1$, the gain control signal will reduce the gain of the variable gain stage 39. On the other hand, if the DC current component of the reference signal is greater than the value of the reference voltage $V_1$, the gain control signal on the conductor 49 will increase the gain of the variable gain stage 39. Thus the difference circuit 47 and the variable gain stage 39 function as an automatic gain control to maintain the voltage of the reference signal at a substantially constant value. Of course since the variable gain stage 39 operates on the composite signal, the automatic gain control circuit 40 reduces the drift effects in both the gas signal and reference signal which result from conditions common to both the cells 17 and 19.

To provide the desired indication of the concentration of the particular gas in the mixture being tested, the reference signal on the conductor 43 can be introduced to the positive input terminal of an operational amplifier 51. The gas signal on the conductor 45 can be introduced through a potentiometer 53 to the negative terminal of the amplifier 51. A resistance 52 associated with the amplifier 51 is variable to adjust the gain of the amplifier 51 to a value such as ten. A different signal is provided at the output of the amplifier 51 to drive a meter 55 the opposite side of which is connected through a potentiometer 57 to a reference potential such as ground 59.

The desirability of calibrating the meter 55 each time the analyzer 11 is used has been previously discussed. This calibration is particularly important to minimize the effects of source emissivity, detector sensitivity, and full time energy absorption along the optical path. Some means of calibration is practially essential to the accuracy of the analyzer 11 since small changes in the magnitude of the output signal can result in significant changes in the deflection of the meter 55.

In the embodiment illustrated in FIG. 1, the calibration of the meter 55 is accomplished by varying the resistance of the potentiometer 53 prior to the introduction of the gas mixture into the gas cell 17. Under these conditions, the signals introduced to the operational amplifier 51 should be substantially equal. Then the signal at the output of the amplifier 51 would be substantially zero so that the meter 55 would provide a zero indication.

Suppose, for example, that the reference signal on the conductor 43 has a mangitude of five volts and the gas signal on the conductor 45 has a magnitude of 10 volts. If the potentiometer 53 is centered, the signals introduced to the amplifier 55 will have an equal magnitude of 5 volts. The different signal at the output of the amplifier 51 would have a magnitude of zero volts so that the meter 55 would provide an indication of zero percent concentration.

It is known that a gas mixture containing a particular percentage of the gas of interest, such as ten percent, will absorb a fixed percentage of the infrared energy, such as 20 percent, in a particular instrument. Thus when the analyzer is initially manufactured, the potentiometer 57 can be adjusted so that the output signal from the amplifier 51 provides the meter 55 with a full scale deflection in response to the particular percentage of gas concentration. After this initial adjustment, the span of the meter 55 will automatically be calibrated when the zero of the meter is calibrated.

If the fixed percentage of the infrared energy absorbed were twenty percent, for example, the gas signal voltage in the exemplary embodiment would be reduced from 10 volts to 8 volts.

If the potentiometer 53 had been centered in accordance with the previous calibration, the modified voltage appearing at the negative input terminal of the amplifier 51 would be four volts. With a reference signal having a magnitude of 5 volts, a difference of 1 volt would be amplified by the gain of the amplifier 51. This gain is typically set by a variable feedback resistance 52 to a gain such as ten. Thus the 1 volt differential would provide the signal at the output of the amplifier 51 with a magnitude of 10 volts.

If the meter 55 had a full scale deflection corresponding to one milliamp, the potentiometer 57 would have initially been set to 10,000 ohms. This would provide the meter 55 with a full scale deflection in response to the 10 volt signal at the output of the amplifier 51. The full scale deflection of the meter 55 would then correspond to the particular percentage of concentration, such as 10 percent, of the particular gas in the gas mixture. It will be noted that no adjustment, other than the zero calibration, is needed to provide the correct span indication. Rather, the parameters of the circuit automatically provide this span condition. Thus the gain span of the meter 55 will always be calibrated with the calibration of the zero adjustment using the potentiometer 53. Separate adjustments need not be made for both the zero and span of the meter 55. Such a calibration circuit can be implemented with only a single knob corresponding to the potentiometer 53 on the face of the analyzer 11. No acess need be provided to the potentiometer 57 once the span adjustment has been set for the particular instrument.

Figure 2:
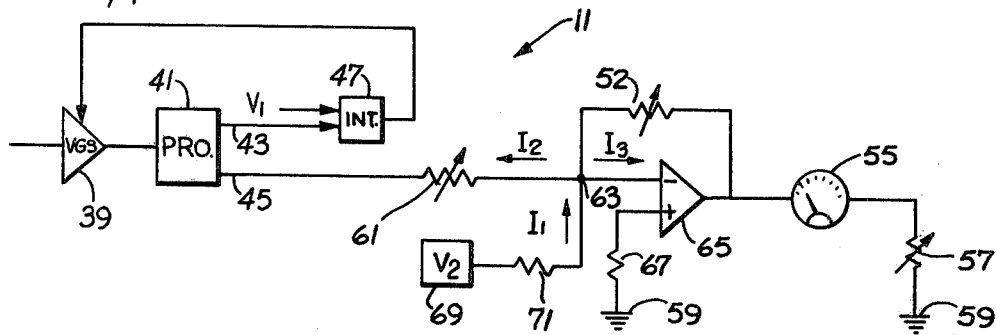
FIG. 2 is a partial schematic of the gas analyzer of FIG. 1 illustrating an additional embodiment of the calibration circuit of the present invention.

In an additional embodiment of the invention, illustrated in FIG. 2, the gas signal on the conductor 45 is introduced through a potentiometer 61, and a particular node 63 to the negative input terminal of an operational amplifier 65. A positive input terminal of the amplifier 65 can be connected through a resistance 67 to the reference potential such as ground 59. Similar to the amplifier 51 in the previous embodiment, the amplifier 65 amplifies the difference in the potentials of the signals on its positive and negative input terminals by a gain such as ten.

In this embodiment, a source 69 providing a voltage $V_2$, is connected through a resistance 71 to the particular node 63. The source 69 and resistance 71 are particularly stable and continually introduce a substantially constant current $I_1$ into the node 63. By way of example, the voltage $V_2$ may have a value such as ten volts and the resistance 71 a value such as 10,000 ohms. This will provide the substantially constant current $I_1$ with a magnitude of 1 milliamp.

The separation of the current $I_1$ at the node 63 is of particular importance to the calibration of the meter 55. A current $I_2$, flowing along the conductor 45 in the direction of the processor 41, will have a magnitude dependent upon the magnitude of the gas signal. A current $I_3$ flowing from the node 63 into the negative input terminal of the amplifier 65 will have a magnitude equal to the difference between the current $I_1$ and the current $I_2$. Since the current $I_1$ is substantially constant, the current $I_3$ will also vary with the magnitude of the gas signal.

Prior to the introduction of the gas mixture into the cell 17, the potentiometer 61 can be varied so that the magnitude of the current $I_2$ is equal to the magnitude of the current $I_1$. Then the magnitude of the current $I_3$ and the signal at the output of the amplifier 65 will be zero. Thus with no gas mixture in the cell 17, the meter 55 can be zeroed by adjusting the potentiometer 61. Assuming again that the current $I_1$ has a magnitude of one milliamp, it might be further assumed that the gas signal has a magnitude of 5 volts. Then the potentiometer 61 could be provided with a resistance of 5000 ohms so that $I_2$ is also equal to 1 milliamp. This would provide the current $I_3$ with the zero magnitude and would provide the meter 55 with a corresponding zero indication.

If the gas signal is reduced by twenty percent as previously assumed to a value such as 4 volts, the potentiometer 61 with a value of five thousand ohms would provide the current $I_2$ with a magnitude of only 0.8 milliamps. Under these conditions, the current $I_3$ would have a magnitude of 0.2 milliamps and the decade gain on the amplifier 65 would provide the signal at its output with the magnitude of 2 volts. The one time calibration of the potentiometer 57 would have provided it with a resistance of 2000 ohms, for example, so that the 2 volts signal would provide a one milliamp full scale deflection for the meter 55. Once again, it will be noted that the zero adjustment corresponding to variations in the resistance of the potentiometer 61 also results in the simultaneous calibration of the span of the meter 55.

Figure 3:
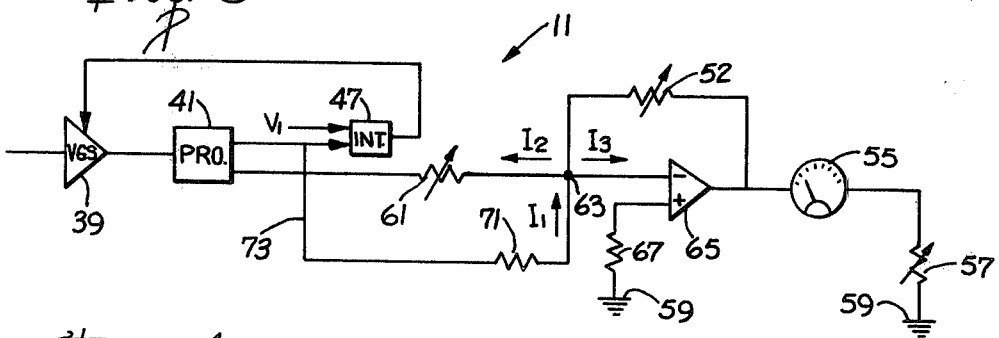
FIG. 3 is a partial schematic of the gas analyzer of FIG. 1 illustrating a further embodiment of the calibration circuit of the present invention.

A further embodiment of the invention is illustrated in FIG. 3. This embodiment is similar to that illustrated in FIG. 2 except for the provision of a conductor 73 which is connected between the conductor 43 and the resistance 71. In this embodiment, the source 69 can be eliminated since the reference signal will provide the voltage associated with the substantially constant current $I_1$.

This embodiment is of particular advantage where the reference signal on the conductor 43 tends to drift slightly in spite of the automatic gain control circuit 40. If the full scale deflection of the meter 55 corresponds to a ten percent variation in the magnitude of the reference signal, then even a one percent change in the magnitude of the reference signal will provide five percent error in the deflection of the meter 55. However, if the drifting reference signal is introduced to the resistance 71 on the conductor 73, the current $I_1$ will vary in a direction to compensate for the drift of the reference signal. For example, if the reference signal drifts one percent low, the gas signal will also drift one percent low. In the embodiment of FIG. 2, these conditions would provide the current $I_3$ with a higher magnitude and the meter 55 with a higher indication. However, in the embodiment of FIG. 3, the currents $I_1$, $I_2$ and $I_3$ would all have magnitudes reduced by one percent so that the meter 55 would provide an accurate indication even with the drift of the reference signal.

Figure 4:
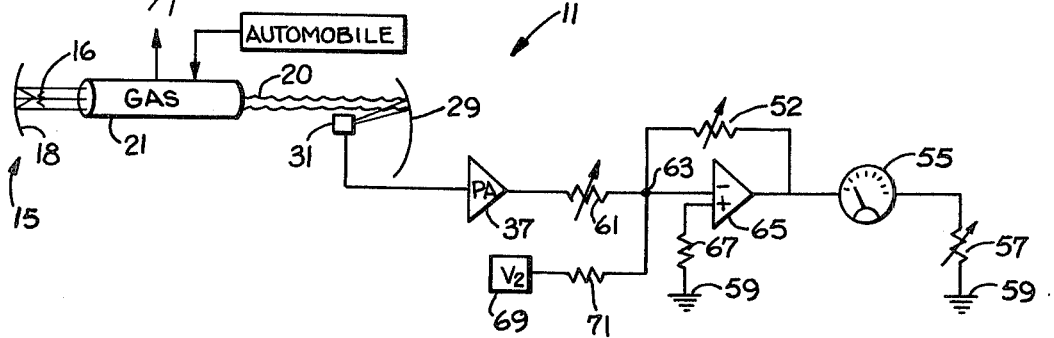
FIG. 4 is a schematic of a gas analyzer having a single gas cell and still a further embodiment of a calibration circuit of the present invention.

The calibration circuits of the present invention will function well in any analyzer which produces a separate signal, such as the gas signal, having a magnitude dependent upon the percentage of concentration of the particular gas in the gas mixture. Thus the calibration circuits of the present invention could be effectively used even in analyzers providing only a single cell such as the gas cell 17. As illustrated in FIG. 4, these analyzers do not include a reference cell such as the cell 19 and therefore can not accommodate an automatic gain control circuit, such as the circuit 40 in FIG. 3. Nonetheless, an independent gas signal is present and the magnitude of that signal can be compared with a fixed reference voltage $V_2$ to calibrate the meter 55.

It is of particular advantage that the disclosed embodiments of the apparatus and method for calibrating an analyzer operate upon the signals following the gas cell 17. There is no attempt to use an expensive and inconvenient calibration gas. Nor is an obstruction or opacity used to block infrared energy to simulate known concentrations of the particular gas being measured. In fact, no external object need be provided for calibration of the analyzer 11. Rather, the magnitude of the gas signal is adjusted to correspond to the magnitude of the reference signal when no gas is being introduced to the cell 17. This condition, which should correspond to a zero percent concentration, can be used to zero the meter 55. The parameters of the calibration circuit can be set to provide for a corresponding full scale deflection in response to a twenty percent reduction in the magnitude of the gas signal. Thus, the zero adjustment automatically provides for the span adjustment in the calibration circuit of the present invention.

The method of the present invention is relatively inexpensive to implement and is relatively accurate. Rather than artificially nulling the output signal developed by either subtracting the reference signal from the gas signal or subtracting the gas signal from a fixed output, the null is accomplished by attenuating or amplifying the gas signal so that it equals either a controlled reference signal or some other carefully controlled standard. In so doing, the gas signal corresponding to a no-gas condition is standardized to a fixed value and from this point, the percentage change in the gas signal has a substantially fixed relationship to the concentration of the gas in the gas mixture.

Although the apparatus and method of the present invention has been disclosed with reference to specific embodiments, it will be appreciated by those skilled in the art that the invention can be otherwise embodied. For example, any of the illustrated embodiments can be modified to function with the comparison of voltages or the summation of circuits. For this reason, the scope of the invention should be ascertained only with reference to the following claims.

I claim:

1. A combination for determining a percentage of concentration of a particular gas in a gas mixture, including:
    a gas cell adapted to receive the gas mixture;
    a source of infrared energy positioned with respect to the gas cell to introduce the infrared energy through the gas cell;
    the particular gas in the cell having properties for reducing the magnitude of the infrared energy emanating from the cell in an amount dependent upon the percentage of concentration of a particular gas in a gas mixture;
    amplifier means having a variable gain;
    first means including the amplifier means for receiving the infrared energy emanating from the gas cell and for providing an electrical signal having particular characteristics dependent upon the percentage of concentration of the particular gas in a gas mixture;
    second means responsive to the electrical signal and having a variable impedance for providing a modified electrical signal having the particular characteristics;
    a reference cell positioned with respect to the source of infrared energy to receive the infrared energy and having a reference gas to provide a particular reduction in the infrared energy emanating from the cell;
    third means including the amplifier means for receiving the infrared energy emanating from the reference cell and for providing a reference signal representative of such infrared energy;
    fourth means for providing a reference voltage;
    fifth means responsive to any difference between the reference voltage and the reference signal from the third means for adjusting the gain of the amplifier means to provide the reference signal with characteristics corresponding to the reference voltage;
    sixth means for comparing particular characteristics of the reference signal and the modified electrical signal and for providing an output signal having at least one characteristic dependent upon the difference of the particular characteristics of the modified electrical signal and the reference signal;
    a meter responsive to the output signal for providing an indication of the percentage of concentration of the particular gas in the gas mixture; and
    seventh means to control the variable impedance of the second means for varying the magnitude of the modified electrical signal to provide the output signal with a particular magnitude representative of the absence of the particular gas in the gas mixture for providing the meter with a zero indication and for calibrating the analyzer for the span of the meter.

2. The combination recited in claim 1 wherein the fifth means provides a feedback path between the output from the third means and the amplifier means for adjusting the gain of the amplifier means in accordance with any differences between the reference signal and the reference voltage and the amplifier means is responsive on a time-sharing basis to the signals representing the output energy from the gas cell and the reference cell.

3. An analyzer for determining the percentage of concentration of a particular gas in a gas mixture, comprising:
    a gas cell;
    a reference cell containing a gas substantially void of the particular gas;
    a source of energy positioned to introduce the energy through the gas cell at first times on a multiplexing basis to provide a first energy signal at the first times and to introduce the energy through the reference cell at second times on the multiplexing basis to provide a second energy signal at the second times;

first means for introducing the gas mixture into the gas cell, the gas mixture having properties for absorbing at least a portion of the energy introduced into the gas cell by the source to provide the first energy signal with characteristics dependent upon the percentage of concentration of the particular gas in the gas mixture;

second means including an amplifier having a variable gain for multiplexing the first and second energy signals and for providing a composite electrical signal on a time-sharing basis;

third means for demultiplexing the composite electrical signal to provide a gas signal having characteristics dependent upon the percentage of concentration of the particular gas in the gas mixture and to provide a reference signal;

fourth means for providing a reference voltage;

fifth means responsive to any differences between the reference voltage from the fourth means and the reference signal from the third means for adjusting the gain of the amplifier means to eliminate any such differences;

variable impedance means for varying the magnitude of the gas signal to provide a modified gas signal;

sixth means responsive to the reference signal and the modified gas signal to provide an output signal having a magnitude dependent upon the difference between the relative magnitudes of the reference signal and the gas signal;

a meter responsive to the output signal to provide an indication of the percentage of concentration of gas in the gas mixture; and means for varying the impedance means for providing the output signal with a zero magnitude for calibrating the analyzer when there is none of the particular gas present in the gas cell and for automatically calibrating the span of the meter.

4. The analyzer recited in claim 3 wherein the sixth means includes a difference amplifier responsive to the reference signal and the modified gas signal to provide the output signal and wherein the fifth means is connected in a closed loop between the third means and the amplifier means.

5. The combination recited in claim 3 wherein the fifth means constitutes feedback means connecting the third means and the second means in a closed loop for adjusting the gain of the amplifier in accordance with any differences between the reference signal and the reference voltage.

6. An analyzer for determining the percentage of concentration of a particular gas in a gas mixture, comprising:

a source of energy providing a beam of the energy;

a gas cell positioned in the beam of the energy and being adapted to receive the gas mixture, the particular gas in the gas mixture having characteristics for absorbing a portion of the energy in the beam to provide an energy signal having a magnitude dependent upon the percentage of concentration of the particular gas in the gas mixture;

a reference cell positioned in the beam of the energy and having a particular gas for absorbing a particular portion of the energy in the beam to provide an energy signal having particular characteristics;

processing means responsive to the energy signal for providing a first electrical signal having a magnitude dependent upon the percentage of concentration of the particular gas in the gas mixture and for providing a second electrical signal in accordance with the energy signal having the particular characteristics from the reference cell;

first means for providing reference voltage;

second means responsive to the reference voltage and the second electrical signal for varying the characteristics of the first and second electrical signals in accordance with any differences in the characteristics of the reference voltage and the second electrical signal;

amplifier means for receiving the first and second electrical signals and for producing a difference signal representing any differences between the first and second electrical signals;

meter means responsive to the magnitude of the difference signal from the amplifier means for providing a visual indication of the percentage of concentration of the particular gas in the gas mixture, the meter means having a zero indication representative of a zero percent concentration of the particular gas in the gas mixture and a span indication representative of a particular percent concentration of the particular gas in the gas mixture; and impedance means operatively coupled to the second means and having a variable impedance for adjusting the magnitude of the first electrical signal relative to the magnitude of the second electrical signal when there is none of the particular gas in the gas mixture in the gas cell to provide calibration of both the zero indication and the span indication of the meter means at the same time.

7. The analyzer recited in claim 6, including multiplexing means included in the processing means and responsive to the first energy signal and the second energy signal to provide a composite electrical signal having characteristics dependent at first particular times upon the magnitude of the first and dependent at second particular times upon the magnitude of the second energy signal; and demultiplexing means included in the processing means and operative in synchronism with the multiplexing means and responsive to the composite signal for providing the first electrical signal and the second electrical signal from the composite signal.

8. The analyzer set forth in claim 7, wherein impedance means are operatively coupled to the amplifier means and are adjustable to vary the gain of the amplifier means.

* * * * *